United States Patent [19]

Espy et al.

[11] Patent Number: 4,751,337
[45] Date of Patent: Jun. 14, 1988

[54] CONVERSION OF SOLID DICYCLOPENTADIENE TO A LIQUID MONOMER FOR USE IN REACTION INJECTION MOLDING

[75] Inventors: Herbert H. Espy, Wilmington; Albert S. Matlack, Hockessin, both of Del.

[73] Assignee: Hercules Incorporated, Wilmington, Del.

[21] Appl. No.: 939,608

[22] Filed: Dec. 8, 1986

[51] Int. Cl.$^4$ .......................................... C07C 175/00
[52] U.S. Cl. .................................................. 585/362
[58] Field of Search ........................................ 585/362

[56] References Cited

U.S. PATENT DOCUMENTS

| | | | |
|---|---|---|---|
| 4,139,569 | 2/1979 | Lane | 585/362 |
| 4,277,636 | 7/1981 | Norton et al. | 585/362 |
| 4,286,109 | 8/1981 | Norton et al. | 585/362 |
| 4,400,340 | 8/1983 | Klosiewicz | 264/328.6 |
| 4,507,453 | 3/1985 | Tom | 526/283 |
| 4,584,425 | 4/1986 | Tom | 585/827 |

*Primary Examiner*—Curtis R. Davis
*Attorney, Agent, or Firm*—William S. Alexander; John P. Luther

[57] ABSTRACT

A method of preparing a mixture composed principally of dicyclopentadiene which is caused to remain liquid at low temperatures by the presence of other cyclopentadiene oligomers.

3 Claims, No Drawings

CONVERSION OF SOLID DICYCLOPENTADIENE TO A LIQUID MONOMER FOR USE IN REACTION INJECTION MOLDING

This invention relates to an improvement in the art of polymerizing dicyclopentadiene to form a substantially crosslinked thermoset polymer having useful properties.

BACKGROUND OF THE INVENTION

U.S. Pat. No. 4,507,453 to Tom and U.S. Pat. No. 4,400,340 to Klosiewicz disclose a new species of thermoset polymers based on dicyclopentadiene monomer which polymers are noteworthy for their unusually good balance of high impact strength and high modulus. These polymers are prepared at low temperatures and under low pressures using a metathesis catalyst system comprising a tungsten or molybdenum catalyst activated by an alkyl aluminum compound. Thanks to the aforementioned unusual balance of modulus and impact strength these polymers based on dicyclopentadiene are commercially desirable materials and they are becoming increasingly sought after for use in molding of shaped articles in complex configurations.

Molding of shaped articles of dicyclopentadiene is carried out by injecting liquid streams of the monomer formulated with catalyst and activator components into an appropriately shaped mold wherein the monomer polymerizes to form the desired shape directly. This can be done via a two-stream process as taught in the cited Tom patent or, with appropriate moderation of the reaction rate, via a one-stream process.

A problem that has been encountered in carrying out the polymerizations as discussed arises out of the fact that dicyclopentadiene melts at 32° C. and is thus a solid at room temperature. Accordingly, it must be heated prior to formulation with catalysts, activators and other additives and must be transported through heat-jacketed lines to maintain a liquid state. A significant process improvement can be effected both in terms of handling ease and plant investment if the monomer can be handled as a liquid at room temperatures and below.

It is known that contaminants or adulterants of many kinds, when incorporated into a solid organic material, depress the melting point by a specific calculable amount. However, most adulterants that might be added to dicyclopentadiene in sufficient amounts to accomplish this reduction interfere with, or even prevent, metathesis polymerization from taking place. Those that doesn't prevent polymerization generally have an undesirable effect on the properties of the polymer.

It is the object of this invention to prepare dicyclopentadiene which is liquid at temperatures below 20° C. wherein the adulterant is an oligomer or a mixture of oligomers of cyclopentadiene which are copolymerizable with dicyclopentadiene. It is a further object to provide a method of preparing the aforesaid adulterated dicyclopentadiene. Yet, another object is to prepare a metathesis polymerizable liquid mixture containing a predominant amount of dicyclopentadiene.

In the description which follows, the term "oligomers" or "cyclopentadiene oligomers" is intended to mean cyclopentadiene oligomers higher than dicyclopentadiene.

BRIEF DESCRIPTION OF THE INVENTION

The objects of this invention are accomplished by a thermal technique wherein dicyclopentadiene is subjected to a temperature of about 125° to 225° C. in the substantial absence of air for about 0.1 to 24 hours under conditions wherein pyrolysis products are prevented from escaping from the reaction and cyclopentadiene oligomers are formed, continuing the heating until the oligomer content is about 5 to 30% of the total weight of dicyclopentadiene plus oligomers and thereafter separating residual low molecular weight pyrolysis products from the dicyclopentadiene/oligomer mixture to form a product which can be polymerized under the influence of a metathesis catalyst system in about 30 seconds or less to form a crosslinked thermoset polymer.

DETAILED DESCRIPTION OF THE INVENTION

In accordance with this invention, dicyclopentadiene is heated in the absence of air under controlled conditions to prepare a defined mixture of dicyclopentadiene and other low oligomers of cyclopentadiene which mixture remains liquid at temperatures below 20° C.

A substantially pure dicyclopentadiene which, in a conventional two-stream metathesis polymerization as described by Klosiewicz, cited above, polymerizes to a substantially crosslinked condition within one-half minute or less and a method of preparing the same is described by Tom in U.S. Pat. No. 4,584,425. Such dicyclopentadiene is 99+% dicyclopentadiene, and this material performs well in the instant invention. It is preferred, but not required that the starting dicyclopentadiene be of such a high degree of purity. Dicyclopentadiene of substantially any reasonable purity level can be employed since the mixture of dicyclopentadiene and oligomers can be purified by the technique taught by Tom.

The thermal or pyrolytic conversion of dicyclopentadiene to higher oligomers is, of course, well known. The reaction proceeds by initial pyrolysis of dicyclopentadiene to cyclopentadiene followed by addition of cyclopentadiene to dicyclopentadiene to form tri-, tetra-, and higher cyclopentadiene oligomers. The reaction has ordinarily been regarded as a nuisance inasmuch as little use is known for these oligomers. In the instant application, the presence of the oligomers is highly desirable as their presence is responsible for depressing the melting point of the dicyclopentadiene to a point at which the liquid state is maintained. Additionally, the oligomers, being strained ring cycloolefins as is dicyclopentadiene, are metathesis polymerizable and copolymerize with dicyclopentadiene to form highly desirable products.

Conversion of dicyclopentadiene to oligomers according to this invention can be effected within a temperature range of about 125° to 250° C. A preferred temperature range is about 135° to 190° and the most preferred is about 140° to 170° C. The time required to carry out the reaction can vary over a wide range depending on the oligomer content desired and also on the temperature range selected. Heating times required to yield the preferred oligomer contents are approximately as follows:

| Temperature | 5–30% Oligomer | 10–25% Oligomer |
|---|---|---|
| 140° C. | 5–60 hrs. | 12–36 hrs. |
| 150° C. | 2–24 hrs. | 5–15 hrs. |
| 170° C. | 0.4–4 hrs. | 1–3 hrs. |
| 190° C. | 0.1–1 hrs. | 0.15–0.75 hrs. |

The process can be carried out in the presence of a hydrocarbon solvent, either aliphatic or aromatic. The aromatic solvents are preferred. More preferred, however, is to carry out the reaction in the absence of any solvent. The reaction proceeds very well in the melt and recovery of the product is facilitated since no solvent removal is required.

The best melting point depression is achieved within the range of about 8 to 30% oligomer content. Below about 5%, the mixture may be liquid at room temperature, but freezes at slightly lower temperatures, leaving only a small temperature range in which to operate. Above about 30%, the mixture begins to resemble an oligomer adulterated with dicyclopentadiene and melting point increases rapidly since the molar freezing point depression constant of the oligomers is much smaller than that of bicyclopentadiene.

The method of the invention, as stated, leads to the formation of tri- tetra-, and higher cyclopentadiene oligomers. For optimum predictability of the characteristics of the polymerization products, it is preferred that the proportion of the tricyclopentadiene relative to other oligomers be as great as possible.

Within the preferred heating temperature range of 140° to 170° C., a time/temperature relationship can be maintained such that the greater portion of the oligomer formed is tricyclopentadiene containing a small amount of tetracyclopentadiene and virtually no oligomers higher than tetracyclopentadiene. Higher temperatures and longer times lead to increased proportions of the oligomers being higher than tricyclopentadiene. Lower temperatures, say 125° C., lead to an even higher proportion of tricyclopentadiene, although at this low temperature, the heating time required is generally regarded as impractical.

In order to make the reaction proceed, it is necessary that it be carried out under conditions such that the cyclopentadiene pyrolysis products, specifically cyclopentadiene, remain within the reaction mass. This is accomplished in most cases by operating under reflux conditions. When operating at temperatures about 140° C., a pressurized system must be used.

Due to the presence of carbon-carbon unsaturation in dicyclopentadiene and also in the oligomers, the system is strongly susceptible to air oxidation. Thus the reaction is carried out in the absence of air and preferably in the presence of an antioxidant. Butylated hydroxytoluene (BHT) is a preferred antioxidant since it has been found to be compatible with the metathesis polymerization system. Other usable antioxidants will be known to the practitioner or can be determined by routine experimentation.

As in most organic chemical processes, there is always a small amount of low molecular weight by-products remaining after the pyrolysis reaction. These are usually low molecular weight, low boiling hydrocarbon materials, a high percentage of which can be unreacted cyclopentadiene monomer. These materials, particularly the cyclopentadiene, will interfere with the metathesis reaction and detract from the physical properties of the polymerization product which results. For these reasons, the by-products must be removed.

Removal of by-products is accomplished by vacuum stripping at relatively low temperature, i.e., about 95° to 105° C. and 50 mm Hg or less. Low temperature stripping is important so that pyrolysis of the previously formed oligomers is minimized. Inert gas sparging at about the same temperature can also be employed. Following the stripping operation, the dicyclopentadiene-oligomer mixture can be contacted with an absorbent such as alumina or a zeolite as taught by Tom in U.S. Pat. No. 4,584,425.

The purified mixture of dicyclopentadiene and oligomer can be polymerized in about 30 seconds or less using the technique of Klosiewicz in U.S. Pat. No. 4,400,340. However, by use of less active activators or more active reaction rate moderators, it is possible to delay the polymerization for substantial periods of time if that is desired. One technique for accomplishing such a delay is disclosed in commonly assigned U.S. patent application Ser. No. 926,272.

The invention is illustrated in the following examples.

EXAMPLES 1 to 12

Aliquots (10 ml) of polymerization grade dicyclopentadiene (99+% pure) were injected into capped, $N_2$-sparged polymerization tubes. These tubes were placed snugly into holes in a cylindrical aluminum block, heated in a heating mantle. Temperature was controlled to ±3° C. by a thermostatic control, monitoring a thermometer in the block. Reaction temperatures were 150°, 170° and 190° C. Zero time was counted when the block reached the specified reaction temperature. Tubes were removed at scheduled times thereafter and allowed to cool to room temperature.

Freezing behavior of the treated dicyclopentadiene was monitored by cooling the tubes in (a) a cold room at 5° C., (b) in ice, (c) in a freezer at −20° C. and (d) in various dry ice solvent baths. Composition of the mixtures was determined by GC analysis with results recorded in Table A.

TABLE A

| Example No. | Temp. °C. | Time Hr[a] | Light Ends | DCPD | Co-Dimers | Cp Trimer | Cp Tetramer | Approx. M.P. °C. |
|---|---|---|---|---|---|---|---|---|
| Control | (Unheated) | | 2.3 | 96.1 | 1.1 | 0.5 | 0.01 | |
| 1 | 150 | 0 | 2.1 | 96.7 | 0.9 | 0.04 | 0.02 | 20 |
| 2 | | 1 | 2.9 | 93.1 | 1.0 | 2.9 | 0.03 | 4 |
| 3 | | 2 | 3.6 | 90.8 | 1.0 | 4.4 | 0.03 | −20 |
| 4 | | 4 | 3.9 | 87.1 | 1.0 | 7.8 | 0.01 | −20 |
| 5 | | 8 | 3.7 | 80.8 | 0.9 | 13.5 | 0.9 | −22 |
| 6 | 170 | 0 | 2.9 | 95.2 | 1.1 | 0.16 | 0.03 | 4 |
| 7 | | 0.5 | 3.8 | 88.0 | 0.9 | 6.8 | 0.3 | −25 |
| 8 | | 1 | 4.2 | 85.2 | 0.9 | 8.8 | 0.6 | −22 |
| 9 | | 2 | 3.7 | 75.6 | 0.9 | 17.8 | 1.7 | −22 |

TABLE A-continued

| Example No. | Temp. °C. | Time Hr[a] | Light Ends | Composition (GC Analysis) | | | | Approx. M.P. °C. |
| --- | --- | --- | --- | --- | --- | --- | --- | --- |
| | | | | DCPD | Co-Dimers | Cp Trimer | Cp Tetramer | |
| 10 | 190 | 0 | 3.8 | 93.8 | 1.0 | 1.2 | 0.02 | −22 |
| 11 | | 0.25 | 3.3 | 76.8 | 0.8 | 16.8 | 2.0 | −22 |
| 12 | | 0.5 | 3.1 | 68.6 | 0.8 | 22.7 | 3.6 | −50 |

[a]Elapsed time after reaching indicated temperature.

EXAMPLES 13 to 16

Several portions (1.5 liter) of the polymerization grade dicyclopentadiene were charged to a nitrogen-flushed agitated flask fitted with a reflux condenser and thermometer with thermostatic temperature controller. The reaction mixture was maintained under nitrogen while nitrogen gas was passed over the end of the reflux condenser with a bubbler. After four hours at 155° C. or 6 hours at 150° C., the mass was cooled, passed through an alumina column under nitrogen and collected in nitrogen-flushed capped bottles containing about 300 ppm (based on the dicyclopentadiene-oligomer mixture) of butylated hydroxytoluene. Half of each preparation was heated to about 35° C. and sparged with nitrogen to remove residual cyclopentadiene and other low boiling materials, then analyzed via Gas Chromotography.

The dicyclopentadiene/oligomer mixtures were polymerized into plaques about 30 cm square and 0.3 cm thick. Physical property measurements were made on these plaques.

The polymerization was carried out as follows:

A 0.5 M solution of tungsten catalyst was prepared by weighing 19.80 g (0.05 mole) of WCl$_6$ under nitrogen into a 200 ml bottle containing a teflon-coated magnetic stirring bar. The tungsten was then slurried in 90 ml of toluene that had been distilled from Na/K alloy under nitrogen. t-Butanol (0.925 g, 0.0125 moles) dissolved in 5 ml of toluene, was added, and the mixture was stirred for one hour while sparging with nitrogen. Nonyl phenol (11.05 g, 0.05 moles) dissolved in 5 ml of toluene was added, and the mixture was stirred for one hour while sparging with nitrogen. Acetylacetone (10.00 g, 0.100 moles) was then added by syringe and the mixture was stirred overnight while sparging with nitrogen to remove HCl gas. Toluene was then added to restore the volume of the solution to its original level and produce a 0.50 M solution.

A 1.0 M solution of complexed aluminum alkyl activator can be prepared by diluting 5.70 g of di-n-octylaluminum iodide, 31.17 g of tri-n-octylaluminum, and 13.42 g of bis(methoxyethyl)ether (diglyme) to a volume of 100 ml with distilled toluene, under a nitrogen atmosphere.

Into 300 ml of heat-treated dicyclopentadiene made by each of the four combinations of temperature—150° and 155°—and sparging (done or not) is added about 4.5 ml of 1 molar aluminum alkyl activator complex and about 3.0 ml of 0.5 molar tungsten complex under a nitrogen atmosphere. After rapid mixing, the resulting solution of catalyst, and activator in dicyclopentadiene is quickly poured into the mold and allowed to polymerize. After the polymerization is complete and the plaque has cooled, the mold is dismantled and the plaque is removed.

Composition data for the dicyclopentadiene/oligomer mixture and properties of the resultant polymer are recorded in Table B.

TABLE B

| | Example Nos. | | | | Untreated Control |
| --- | --- | --- | --- | --- | --- |
| | 13 | 14 | 15 | 16 | |
| Preparation | | | | | |
| Heat Cycle Temp. °C. | 155 | 150 | 150 | 155 | |
| Heat Cycle Time | 4 | 6 | 6 | 4 | |
| N$_2$ Sparged Afterwards | no | no | yes | yes | |
| Analyses | | | | | |
| Light Ends (incl. Cp* monomer), % | 0.29 | 0.33 | 0.23 | 0.08 | 0.06 |
| DCPD, % | 88.4 | 88.6 | 87.8 | 88.9 | 98.3 |
| Cp trimers, % | 9.9 | 10.2 | 11.0 | 10.4 | 1.6 |
| Cp tetramers, % | 0.5 | 0.4 | 0.6 | 0.5 | 0.01 |
| Freezing Tests (°C.) | | | | | |
| All liquid | −9° C. | −9° C. | −5° C. | −5° C. | 30° C. |
| Amt frozen at −8° C. | | | 40% | 80% | 100% |
| Amt frozen at −16° C. | 80% | 70% | | | |
| Amt frozen at −20° C. | 100% | 100% | 100% | 100% | |
| Polymer Properties | | | | | |
| Tg, °C. | 133 | 135 | 138 | 148 | 110–115 |
| Residual Monomer, % | 2.30 | 2.15 | 1.54 | 1.28 | |
| Mechanical Properties | | | | | |
| Flex Modulus, GPa | 2.29 | 2.30 | 2.27 | 2.22 | |
| Flex Strength, Mpa | 90.9 | 90.9 | 87.5 | 88.5 | |
| Plate Impact, Joules | 4.05 | 3.77 | 4.16 | 1.30 | |
| Notched Izod, J/m | 215 | 199 | 211 | 69 | |

*Cp = cyclopentadiene.

EXAMPLE 17

Polymerization grade dicyclopentadiene was heated in a steel autoclave under a nitrogen atmosphere at 145° C. for 6 to 9 hours or 165° C. for 3 to 5 hours. The heat-treated dicyclopentadiene was then vacuum stripped at about 50 mm Hg, at pot temperatures from about 98° to about 108° C., giving material with the analyses and freezing points shown in Table C.

The stripped, heat-treated dicyclopentadiene was polymerized using a tungsten catalyst at a monomer/W-/Al mole ratio of 1000/0.625/1.87, on a reaction injection molding machine supplied by Accuratio Company, Jeffersonville, Ind.

The dicyclopentadiene/oligomer containing 6% by weight of styrene-butadiene random copolymer rubber was added to both tanks. Sufficient tri-n-octylaluminum was transferred into the A tank so that the concentration was 0.0226 M. Sufficient dioctylaluminum iodide was added so that its concentration was 0.0040 M. Sufficient dimethoxyethyl ether (diglyme) was added so that the ratio of diglyme to aluminum alkyl was 1:1. Next, sufficient tungsten catalyst solution was added to the B side tank to bring the concentration of catalyst to 0.0089 M. All transfers were done and all materials were handled in a way to preclude the entrance of oxygen or moisture into the system. The materials were then thoroughly blended in their respective tanks.

The activator and the catalyst stream were mixed in a standard impingement type RIM mixhead. The ratio of the activator/monomer solution mixed with the catalyst/monomer solution was 1:1. The impingement mixing was accomplished by passing both the solutions through orifices 0.081 cm in diameter at a flow rate approximately 80 ml/sec. This required pumping pressures of approximately 1000 psi.

The resulting mixture flowed directly into a mold heated to between 50° and 60° C. The mold had a flat cavity that forms a plaque sample 10"×10"×⅛" thick. The mold was opened and the finished plaque was removed approximately 30 seconds after the mold was filled.

Mechanical property measurements of the polymerization products are shown in Table C.

TABLE C

| Designation: XD-95 | Dicyclopentadiene Treatment and Composition | | | |
|---|---|---|---|---|
| | 18 | 19 | 20 | 21 |
| Heating Temperature, °C. | 145 | 145 | 165 | 165 |
| Heating Time, hr. | 6 | 9 | 3 | 5 |
| Composition After Stripping, % | | | | |
| Cp* Monomer | 0.02 | 0.06 | 0.03 | 0.06 |
| DCPD | 93.5 | 89.7 | 83.3 | 76.4 |
| Cp Trimer | 6.5 | 10.2 | 16.1 | 22.2 |
| Cp Tetramer | — | — | 0.6 | 1.3 |

TABLE C-continued

| Freezing Point, °C. | 6.4 | −30 | −28 | −30 |
|---|---|---|---|---|
| | Poly(dicyclopentadiene) | | | |
| Tg, °C. | 132 | 141 | 152 | 162 |
| Heat Distortion | | | | |
| Temp., °C. | 88 | 98 | 109 | 118 |
| % Swell | 100 | 90 | 84 | 80 |
| Mechanical Properties | | | | |
| Flex Modulus, GPa | 1.94 | 2.09 | 2.04 | 2.14 |
| Flex Strength, MPa | 78 | 85 | 87 | 90 |
| Tensile Modulus, GPa | 1.59 | 1.61 | 1.61 | 1.63 |
| Tensile Strength, MPa | 41 | 45 | 44 | 48 |
| Elongation, % | 79 | 60 | 39 | 50 |
| Plate Impact, Joules | 21.0 | 19.8 | 17.4 | 13.2 |
| Notched Izod, J/m | 384 | 281 | 198 | 133 |

*Cp = cyclopentadiene

What I claim is:

1. A method of preparing a methathesispolymerizable liquid mixture containing predominantly dicylopentadiene which comprises subjecting dicylcopentadiene to a heat treatment at about 125° C. to 250° C. in the substantial absence of air under conditions wherein pyrolysis products are prevented from escaping from the reaction and cyclopentadiene oligomers are formed, continuing the heating until the cyclopentadiene oligmer content is about 5 to 30% by weight of the total weight of dicyclopentadiene plus oligomers and spearating residual cyclopentadiene and low molecular weight pyrolysis products from the dicyclopentadiene and oligmer mixture thereby recovering dicyclopentadiene and oligomers which can be polymerized under the influence of a metathesis catalyst system in about 30 seconds or less to form a crosslinked thermoset polymer.

2. The process of claim 1 wherein the heat treatment is carried out at about 140° C. to about 170° C.

3. The process of claim 2 wherein the heat treatment is carried out in the absence of a solvent.

* * * * *